United States Patent [19]
Yung

[11] Patent Number: 5,308,589
[45] Date of Patent: May 3, 1994

[54] ODOR CONTROL SYSTEM

[75] Inventor: Shui-Chow Yung, Encinitas, Calif.

[73] Assignee: Calvert Environmental, Inc., San Diego, Calif.

[21] Appl. No.: 811,833

[22] Filed: Dec. 20, 1991

Related U.S. Application Data

[63] Continuation-in-part of Ser. No. 690,672, Apr. 24, 1991, abandoned.

[51] Int. Cl.[5] .............................................. B01D 50/00
[52] U.S. Cl. ...................................... 422/169; 422/5; 422/168; 96/53; 95/65
[58] Field of Search ........................ 422/5, 168, 169; 261/116; 55/8, 10, 122

[56] References Cited

U.S. PATENT DOCUMENTS

| | | | |
|---|---|---|---|
| 3,258,308 | 8/1965 | Peterson et al. | 423/215.5 |
| 3,643,623 | 2/1972 | Eng et al. | 55/8 X |
| 4,070,424 | 1/1978 | Olson et al. | 261/142 |
| 4,194,888 | 3/1980 | Schwab et al. | 55/2 |
| 4,247,308 | 1/1981 | Calvert et al. | 55/8 |
| 4,271,134 | 6/1981 | Teller | 71/34 |
| 4,619,670 | 10/1986 | Malcolm et al. | 55/107 |
| 4,678,481 | 7/1987 | Diep | 55/4 |
| 4,885,139 | 12/1989 | Sparks et al. | 422/169 |
| 4,957,512 | 9/1990 | Denisov et al. | 55/8 |
| 5,085,673 | 2/1992 | Bentley et al. | 55/10 |

Primary Examiner—Robert J. Warden
Assistant Examiner—Krisanne M. Thornton
Attorney, Agent, or Firm—William Patrick Waters

[57] ABSTRACT

An odor control system includes an inlet section of a chamber for spraying waste gas with a suitable reactive chemical agent, for odor removal purposes. An electrostatic precipitator is mounted downstream of the inlet section, within the chamber, for removing chemical residues. The electrical field strength of the electrostatic precipitator is adjustable as needed, to satisfy operating system requirements.

12 Claims, 2 Drawing Sheets

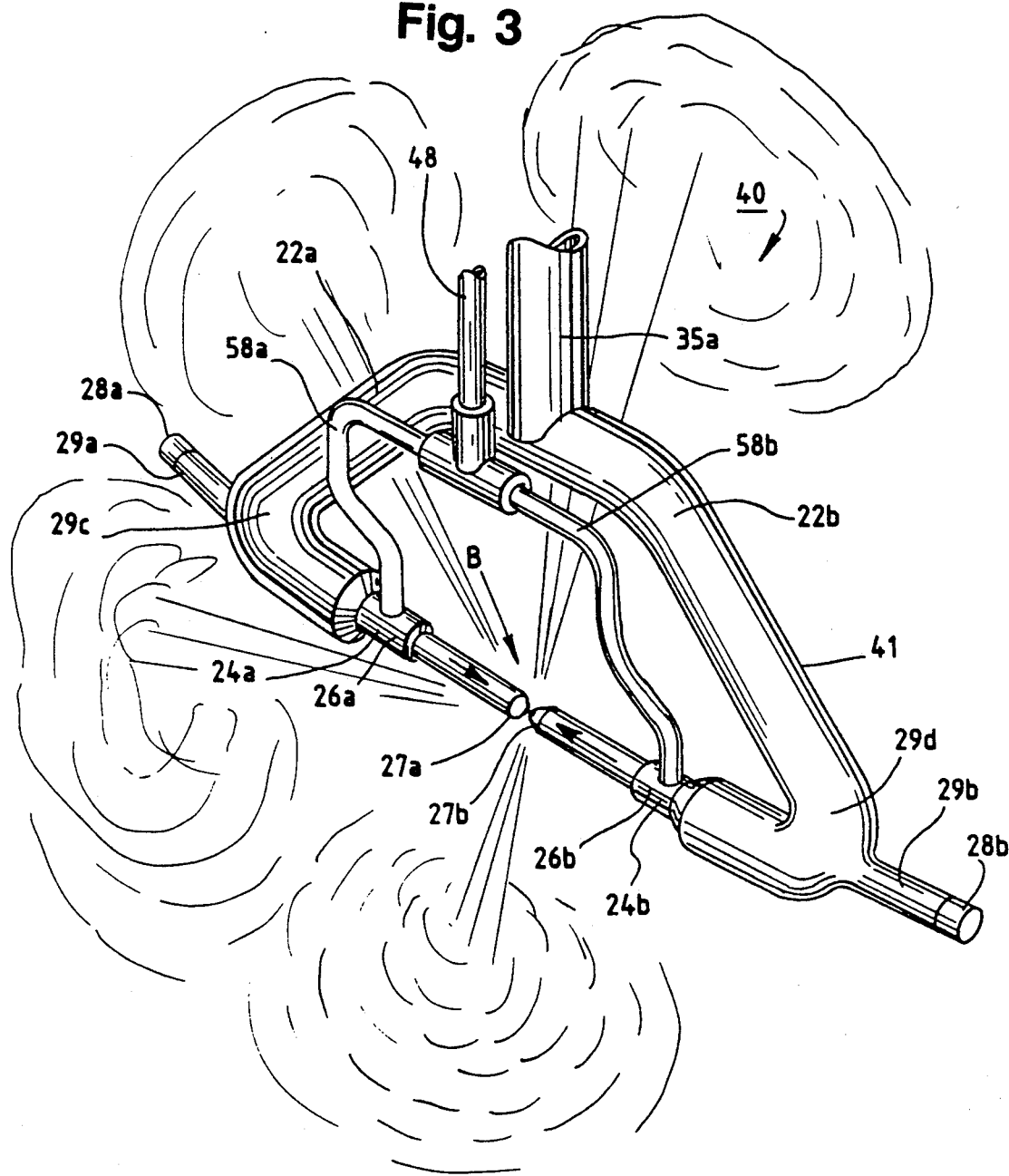

ODOR CONTROL SYSTEM

CROSS-REFERENCE TO RELATED APPLICATIONS

This patent application is a continuation-in-part patent application of copending application Ser. No. 07/690,672, filed Apr. 24, 1991, and now abandoned entitled "Wet Electrostatic Precipitator and Method of Using Same," which is incorporated herein by reference as if fully set forth herein.

DESCRIPTION

1. Technical Field

The present invention relates generally to odor control systems and methods of using them. More particularly, the invention relates to an odor control mist scrubber for effluent waste gases.

2. Background Art

For decades, effluent waste gases from various industrial processes, incinerators, sewer beds, rendering plants and the like, have presented serious pollution control problems. This is especially true in recent times when, with a growing worldwide population, urban centers are located in proximity to the sources of production of unwanted, malodorous waste gases. In recognition of the need for removal of unwanted contaminants from waste gas streams, various methods have been developed. In general, the method utilized is tailored to the type of contaminant to be removed.

Frequently, the pollutants are in the form of air borne particles, carried in a waste gas stream emanating from sewer beds and certain industrial processes, such as rendering plants. The particles range in size from relatively large particulates, as seen in flue gases from incinerating operations, to minute particles, sometimes of submicron size, which are developed by rendering plants, sewage treatment plants, and the like.

In the case of the larger flue gas contaminants, wet scrubbers have been utilized for treating the gas and removing the particulates. In a typical wet scrubber, particle removal is achieved when water under pressure is sprayed into a treatment chamber containing the flue gas. The removal phenomenon is generally mechanical, rather than chemical, in nature. Large orifice nozzles, producing large droplets, are suitable, since large aqueous surface areas are not required for mediating chemical reactions. For example, in U.S. Pat. No. 4,305,909, there is disclosed an integrated flue gas processing apparatus including an integrated system utilizing a spray scrubbing tower and a wet electrostatic precipitator.

Other conventional systems, utilizing various gas treatment methods are disclosed in U.S. Pat. Nos. 3,363,403; 3,331,192 and 4,256,468. In general, these systems are highly complex and expensive.

In sharp contrast to such wet scrubbers, such systems are not designed for small particle removal, such as the particle removal requirement for odor control of waste gas treatment. It is not unusual, when such small particles are required to be removed, that conventional odor control systems can be expensive, complex and, in some cases, not very effective.

Wet scrubbing systems are generally not designed for small particle removal, and are designed to operate on hot flue gases. Thus, they are limited in their industrial applications.

In addition to the limitations of the foregoing mentioned conventional odor control systems, there is a problem of unreacted agents being released into the atmosphere. Additionally, in prior known conventional systems, compressed air is used to drive a finely divided water/chemical mixture into a reaction zone, for treating the waste gas. Because compressed air is relatively dry, the water vapor/chemical reagent drops evaporate quickly within the mist scrubbing system, thereby producing a chemical residue. The residue, typically very small particles having a mass median diameter in the order of two microns or less, frequently includes either reactant products or unreacted substances. They may be acidic, or basic, in nature.

Because of the small size of the particles, the residue is generally beyond the removal capability of conventional mist scrubbers. As a result, the chemical residue frequently passes inadvertently into the atmosphere with the treated waste gas.

Thus, while conventional mist scrubbing systems are satisfactory for some applications, the chemical residue passing into the environment has unwanted and undesirable effects on the environment. In addition, in some cases, the residue may present a public health threat to those in proximity to the mist scrubber.

In view of the foregoing, it would be highly desirable to have an odor control apparatus, and method, which would be capable of small particle removal in a safe, efficient and economical manner, and which would reduce substantially the amount of chemical residue released into the atmosphere. Such a system and method should be less complex than conventional odor control systems.

In U.S. Pat. No. 4,125,589 there is disclosed an odor control system for treating gases containing offensive constituents. The gas is passed through a spray treatment zone where the gas is contacted by a finely divided spray, of water and an oxidizing agent. While such a method may remove some odoriferous constituents, it presents several significant drawbacks. For example, because of an emphasis on removing odor from the gas, no oractical limits are placed on the volume of oxidizing agent utilized in the process. As a result, an excess of such agent is often used with resulting economic waste and otherwise undesirable results.

In addition, the unreacted treating agents may represent a substantial health hazard when they are released into the atmosphere. For example, it is recognized that some agents, such as bleaches, containing sodium hypochlorite, can be potential hazards if released in unreacted form into the atmosphere In the case of sodium hypochlorite, the danger of hydrogen chloride formation, after discharge from the stack, is a serious concern.

Often, a surplusage of unreacted reagents released to the atmosphere form a visible plume exiting the smokestack. In such a situation, the gas leaving the stack may be odor free. However, the plume may contain substantial amounts of unreacted noxious particles being released to the atmosphere. Thus, for example, while the U.S. Pat. No. 4,125,589 discloses a method for removing odoriferous constituents from a waste gas stream, the patented technique does not address the unreacted reagent problem.

In some prior known systems, levels of bleach are reduced, in a manual operation, when a plume is visually observed by an attendant. Such an attempt to control the release of pollutants is satisfactory for many applications. However, in some situations, such as during night operations, observation of the plume may be difficult if not impossible. The net result is that the gas being treated may no longer be odoriferous, but the atmosphere can become polluted to an unacceptable level in such circumstances. In view of the foregoing, it would be highly desirable to have an apparatus and method capable of removing unwanted contaminants from a gas stream, while significantly controlling the amount of unreacted treating agents released into the atmosphere.

With regard to another conventional process, U.S. Pat. No. 4,994,245 discloses a method for removing odors from process air streams by using sulfuric acid and surfactant materials introduced into an air stream. In addition, bleach is utilized for odor removal, and attempts are made to remove odoriferous constituents and noxious particles from the resulting plume. In spite of these efforts, even after the treatment process is completed, unwan.ted constituents still remain in the gas stream.

In an attempt to deal with such unwanted costituents, the process disclosed by U.S. Pat. No. 4,994,245 requires a dilution fan at the stack to dilute the air stream, thereby making the plume less visually discernable. Of course, the problem of release of unreacted constituents into the atmosphere remains, because the absolute amount of particle discharge is the same. Thus, only a superficial attempt to conceal the existence of the plume has been accomplished, and unreacted substances such as sodium hypochlorite, are continuously inadvertently discharged into the atmosphere during operation of the process.

In addition to the above limitations with regard to the inability to remove sufficient quantities of unwanted constituents from the plume, the last mentioned patent discloses a process requiring three stages of treatment and recirculation of reagents. Thus, a large facility, requiring expensive treatment chambers, plumbing, pumps and reagent containers are all necessary to implement the patented system. As a result, the process is unduly complex and expensive to manufacture. Further, such a process is dependent upon the proper functioning of all components at all times. If a single component of one of the three stages fails, the entire process becomes inoperative.

Thus, it would be desirable to have an odor control system having a much more simplified design. Such a system should be less dependent on proper simultaneous, multistage functioning of complex components.

Another significant drawback of the process disclosed in the last mentioned patent, is the requirement for use of sulfuric acid. The use of such a strong acid can constitute a potential hazard, due to its highly corrosive and caustic characteristics. Thus, utilization of such an acid requires expensive safety precautions and highly trained personnel, thereby adding significantly to system operating costs.

In summary, it will be noted that some conventional systems may efficiently remove odor from waste gas streams, but unreacted noxious particles can be left untreated by the process, only to form an unwanted, noxious plume, which passes into the atmosphere. While some attempts may have been made to dilute the undesirable plume, thereby covering up the release of unwanted particles, sufficient particle removal is not accomplished for many applications. In addition, conventional odor control systems are not entirely effective for monitoring plume constituents so that potentially hazardous constituents, such as unreacted sodium hypochlorite, can pass freely into the atmosphere.

In view of the foregoing, it would be highly desirable to have a new and improved odor control system, which could remove odoriferous constituents from waste gas streams, at the same time greatly reducing the amount of unreacted constituents being released into the atmosphere. Such a system should operate in a less expensive, less complex and safer manner than conventional odor control systems.

DISCLOSURE OF THE INVENTION

The principal object of the present invention is to provide a new and improved odor control system and the method of using it, for removing unwanted substances from waste gases, while substantially reducing the amount of unreacted reagents discharged into the atmosphere.

Another object of the present invention is to provide such an odor control system, which is relatively inexpensive to manufacture, easily installed and requiring little maintenance.

Briefly, the above and further objects of the present invention are realized by providing an odor control system which includes an inlet section for spraying waste gas with a suitable reactive chemical agent, for removing odors from the gas, and an electrostatic precipitator mounted downstream of the inlet section for removing chemical residues.

The inlet section includes a pair of oppositely disposed, spaced apart spray nozzles which direct their spray of chemical agent toward one another for achieving a highly efficient and effective mode of operation.

The electrical field strength of the electrostatic precipitator is adjustable as needed, to satisfy operating system requirements. Since the field strength can be varied, the life of the precipitator is prolonged and a capability for adjustment to varying conditions is provided.

A distinct advantage of the present inventive system is that it not only removes unwanted substances from waste gases, but it also eliminates the discharge of unwanted chemical residue into the environment in a highly efficient manner. Also, the inlet section includes a spraying arrangement which includes a pair of spray patterns for a more efficient and effective operation.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 3 is an enlarged pictorial view of a mist nozzle assembly of the system of FIG. 1.

BEST MODE FOR CARRYING OUT THE INVENTION

Figure 1:
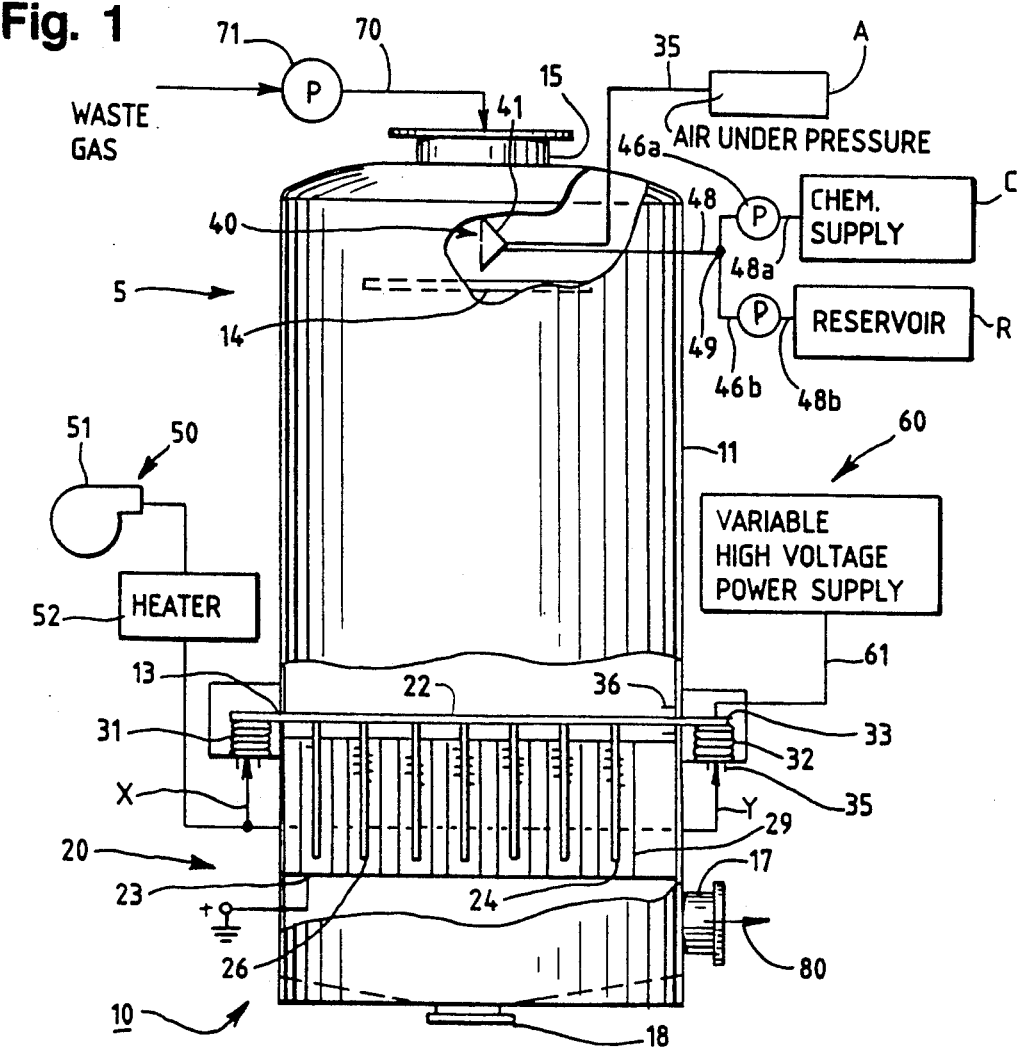
FIG. 1 is a fragmentary, diagrammatic view of an odor control system, which is constructed according to the present invention.

Referring now to the drawings, and more particularly to FIG. 1 thereof, there is shown a new odor control system 10, which is constructed in accordance with the present invention.

The system 10 generally comprises an inlet section 15 of a mixing chamber 11 for spraying a suitable reactive chemical agent, for odor removal purposes, and has a waste gas entrance or inlet 15 for delivering to the interior of the chamber waste gas via a conduit 70, by means of a pump 71. An electrostatic precipitator 20 disposed downstream of the inlet section removes chemical residues from the sprayed waste gas.

The inlet section 15 includes a spray nozzle assembly 40, disposed within the chamber 11. After passing through the precipitator 20, the gas undergoing treatment exits the chamber 11 through a conduit or outlet 17 in the form of a treated gas as indicated by the arrow 80. The treated gas is conveyed via the conduit 17 to a stack (not shown) for discharge into the atmosphere. Residue, in the form of particulate matter, separates from the gas stream and can be removed through an outlet 18, at the bottom of the treatment chamber 11.

With regard now to the spray nozzle assembly 40, in reference to FIGS. 1 and 3, the nozzle assembly 40 is used as the reactive solution droplet producing means in the odor control system of the present invention. The nozzle assembly 40 mixes reagents such as sodium hydroxide or other bleach like substahces from a chemical supply C (FIG. 1) with water from a reservoir R (FIG. 1) to form a chemical treatment solution.

Water is pumped through a line 48 by a pump 46*a*, while bleach is pumped through a line 48*b* by a pump 46*b*. The lines 48*a* and 48*b* join at a tee 49 through which an aqueous mixture of bleach and water flows through a line 48 into the nozzle assembly 40. The mixture is driven through the nozzle assembly by a compressed carrier gas from a gas source A which is delivered to the nozzle assembly 40 through a line 35 (FIG. 1). Suitable bleach like substances, for various operations, may be sodium hydroxide, sodium hypochlorite, sulfuric acid and hydrogen peroxide. In some applications one of the substances may be used, while combinations of the substances may be appropriate for other applications.

As best seen in FIG. 3, during operation of the nozzle assembly 40, the carrier gas, such as compressed air, enters a generally triangular shaped nozzle conduit 41 from a carrier gas line 35*a*, divides into two carrier gas stream via a pair of downwardly converging air manifolds 22*a* and 22*b*, and exits from a pair of horizontally inwardly turned portions having a pair of Venturi nozzles 24*a* and 24*b* including throats 26*a* and 26*b*. The nozzles are positioned in a spaced apart, opposed manner to direct their sprays into direct opposition with one another, as indicated in the drawings.

The throats of the Venturi nozzles have an inner diameter, ranging from ¼ to ¾ inch, depending on chemical solution flow rate, and the gap of the nozzle outlets 27*a* and 27*b* ranges from 178 to 1 times the Venturi throat diameter, thereby lessening the plugging problems sometimes associated with conventional pneumatic spray nozzles. In this regard, the nozzle assembly 40 includes plugs 28*a* and 28*b* which are threadedly engageable in the threaded openings of extensions 29*a* and 29*b*. The extensions 29*a* and 29*b* communicate with U-shaped conduits 29*c* and 29*d*, with the extensions 29*a* and 29*b* preferably linearly aligned with the Venturi nozzles 24*a* and 24*b* respectively. The plugs can be easily removed by conventional methods, such as by use of a wrench (not shown), and a resilient bristle tube brush (not shown) can be inserted for easy cleaning of the Venturi nozzles.

The carrier gas flows through the air manifolds, 22*a* and 22*b* varies according to the amount of treatment solution to be atomized. Typically, 30-500 cfm of the carrier gas flowing at about 10-30 psi is suitable.

Treatment solution is preferably injected radially inward through treatment solution injection lines 58*a* and 58*b* at the Venturi nozzle throat entrances 26*a* and 26*b*, respectively. The treatment solution is injected through the injection lines 58*a* and 58*b* at a rate of about 0.1 to about 2.0 gallons/minute. The primary atomization of the liquid treatment solution occurs at the Venturi throats, where the liquid is entrained by the high velocity carrier gas and shattered into droplets having a diameter of about 50 to about 100 microns.

After flowing past the Venturi throats, the primary atomized gas treatment solution mixture accelerates from zero to the gas velocity in the throat, which ranges from about 200 to about 1000 ft. per second. The two streams are directed at each other so they collide head-on in a second atomization or collision zone B between the outlets 27*a* and 27*b* of the Venturi nozzles 26*a* and 26*b*. As a result of the collision, the relative velocity of the opposing carrier gas streams increases to at least about twice the maximum value the streams had in the Venturi throat. The relatively large drops formed in the Venturi throats are no longer stable. As a result, they undergo a secondary atomizatioh and shatter into much smaller droplets (5-20 microns) yielding a large cloud. The fine droplets result in greater contaminant mass transfer between the waste gas and the treatment solution droplets.

The cloud has a unique rough shape (phantom lines in FIG. 3) due to the physics of the collision. In this regard, the droplets are dispersed radially perpendicular to the linearly aligned Venturi nozzles, and preferably also radially perpendicular to the direction of the incoming waste gas stream to help the mixing of the chemical fog and the waste gas. It should be appreciated that although the preferred embodiment of the present invention includes linearly aligned Venturi nozzles, non-linear alignment is also within the scope of the present invention so long as a cloud containing fine droplets is produced.

A baffle plate 14 having a diameter equal to about ½ the treatment chamber 11 inner diameter is disposed within the treatment chamber 11 downstream from the spray nozzle assembly 40. The baffle 14 provides a means for increasing mixing between the impaction cloud formed by the spray nozzle assembly 40 and the waste gas stream 70.

After the air stream 70 has undergone treatment by the spray nozzle assembly 40, the gas flows to the precipitator assembly 20 for particle removal. The electrostatic precipitator is more fully described in copending U.S. patent application Ser. No. 07/690,672, filed Apr. 24, 1991, which is incorporated herein by reference.

With specific reference to the electrostati precipitator 20 of the present invention, the precipitator 20 comprises a bus bar 22 concentrically disposed within the treatment chamber 11 and passing through an opening 13 in the treatment chamber 11 into an insulator compartment 30 wherein it is supported bY insulated supports such as the supports 31 and 32.

The bus bar is disposed within a housing 23 within the chamber 11. Arrayed along the length of the bus bar 22 in the mixing chamber 11 is a plurality of elongated electrodes 24 and 26, each of which is disposed coaxially within a tube, such as the tube 29. The tubes are electrically connected to the housing 23 and the electrodes are attached to the bus bar 22 by electrically conductive connectors, such as the connector 28 of FIG. 2. Each oft he electrodes, such as the electrodes 24 and 26, is axially positioned on the bus bar 22 parallel to the flow of the air stream within the treatment chamber 11.

During operation of the odor control system 10 of the present invention, a variable high voltage power supply 60 for charging the electrodes, such as the electrodes 24 and 26, is connected to one end of the bus bar 22 within the insulator compartment 30 by means of an electrical power line 61. It is known that in the use of conventional electrostatic precipitators, a voltage which is too high causes arcing between the electrodes. Such a condition is unnecessarily wasteful of electrical energy and, in addition, it shortens electrode life.

Thus, a voltage which is too high is not economically feasible in many operations. When the voltage is too low, on the other hand, the system is inefficient and ineffective in particle, removal. The voltage power supply 60 of the present invention is variable so that, during odor control system 10 operation, the voltage to the bus bar 22 is adjustable. In this regard, the operator is able to adjust the voltage to a level just short of arcing so as to produce a predetermined number of sparks per minute.

During operation of the odor control system 10, the treated gas, containing particulate chemical reaction products and unreacted reagents, flows past the electrodes, such as the electrodes 24 and 26. A voltage of about 4 to about 7 kV/cm is delivered to the electrodes to ionize the particles and remove them from the gas stream. In a preferred form of the present invention, a wet electrostatic precipitator 20 having a collection area from about 80 to about 120 square feet per one thousand cubic feet of waste gas, operated at a field strength of 4-7 kV/cm, is suitable for particulate removal and elimination of a visible plume. During maintenance of the odor control system 10, ionized particles adhering to the electrodes 24 and 26, as well as sludge and particulate matter accumulating at the bottom of the treatment chamber 10, can be washed down with a stream of water and removed from the treatment chamber 11 through the outlet 18.

Figure 2:
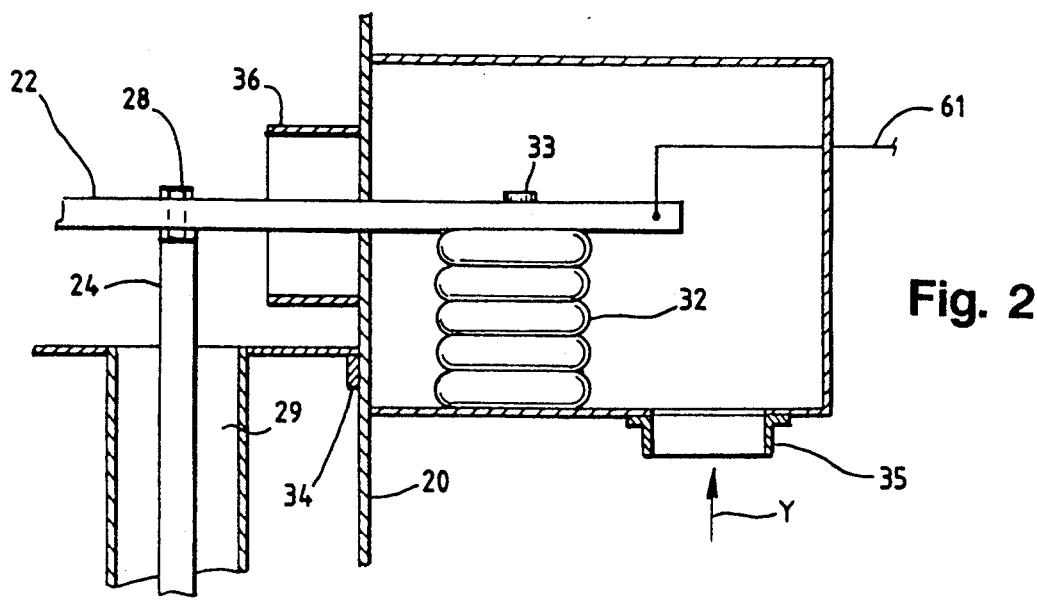
FIG. 2 is an enlarged fragmentary sectional view of a portion the system of FIG. 1.

As shown in FIG. 2, surrounding each electrode, such as the electrode 24 is a collector tube 29, adapted for deposition therewithin of particulate matter. Each of the collector tubes, such as the collector tube 29, is aligned in such a manner that each adjacent collector tube is connected electrically and the entire group of collectors is supported at each end to the inner wall of the treatment chamber 11 by means of a support 34.

With further reference to FIGS. 1 and 2, a purge air system 50, comprising a fan 51 and an in-line heater 52, supplies heated dry air to the insulator compartment 30 through inlets 35 and 35a, to reduce the moisture content within the compartment. The heated air is delivered at X and Y (FIG. 1) to the insulator compartment 30 and it flows out of the compartment 30 through an outlet 36 from whence it flows along the bus bar 22.

Thus, by the utilization of the opposed nozzle assembly 40, and the precipitator, a highly efficient and effective odor control mode of operation is achieved. The efficiency is so high that the level of unreacted chemical residue is highly satisfactory for many applications, and yet the system and method of the present invention is not overly complex.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A system for processing waste gas containing odoriferous contaminants comprising:
    an elongated vertical chamer having an inlet, an outlet and an elongation axis, said inlet being disposed above the outlet, said chamber having means defining a treatment zone between the inlet and the outlet;
    means for flowing a waste gas under pressure into the inlet of said chamer and for directing the flow of the gas under pressure toward the treatment zone;
    means disposed at the treatment zone for spraying an additive under pressure into the treatment zone;
    said means for spraying includes; first and second conduits for guiding the additive, each of said conduits having at least one discharge nozzle adjacent one end thereof, the discharge nozzle on the first conduit arranged in a spaced apart and directly opposed configuration with respect to the at least one discharge nozzle on the second conduit such that theflow path of the discharge from the first conduit directly intersects the flow path of the discharge from the second conduit thereby to produce a discharge cloud extending radially perpendicular to the elongation axis;
    electrostatic precipitor means having a plurality of grounded electrode tubes mounted within said chamber, for ionizing chemical reation products for removal thereof from the gas under pressure flowing to the outlet wherein each of said tubes has a concentraically disposed electrode wherein the concentric electrode attracts the ionized products as the gas passes vertically, downwardly through the electrode tubes; and
    means disposed at said outlet for discharging substantially odor free gas to the atmosphere.

2. A system of claim 1, wherein said spraying means is intermediate said inlet and said treatment zone.

3. A system of claim 1, wherein said electrostatic precipitator means includes an electrically chargeable bus bar and at least oen discharge electrode electrically and mechanically attached thereto.

4. A system of claim 3, including means for providing a dry purging gas to said bus bar to maintain said bus bar in a substantially dry condition.

5. A system fo claim 1, including access means for cleaning said chamber wherein said means are disposed between said electrostatic precipitator means and said outlet.

6. A system of claim 1, inlcuding variable voltage power supply means for supplying voltage to said electrostatic precipitator means.

7. A system according to claim 1, wherein said electrostatic precipitator means includes a plurality of discharge means disposed with a housing.

8. A system according to claim 1, wherein the inner diameter of said at least one discharge nozzle is about ¼ inch to ¾ inch.

9. A system according to claim 1, wherein each conduit includes plug means and a tube having one end in fluid communication with the at least one discharge nozzle having the other end and constructed and arranged to receive the plug wherein the tube is linearly aligned with the conduit.

10. A system of claim 1 including means for supplying a carrier gas to the conduts.

11. A system of claim 1 including reservoir means for storing said additive wherein said reservoir means ar in fluid communication with the conduits.

12. A system of claim 1 including means for supplying a reactive compound to the conduits.

* * * * *